US008014858B1

(12) United States Patent
Ben-Haim et al.

(10) Patent No.: US 8,014,858 B1
(45) Date of Patent: Sep. 6, 2011

(54) SHOCKLESS DEFIBRILLATION

(75) Inventors: Shlomo Ben-Haim, Cessaria (IL); Nissim Darvish, Haifa (IL); Yuval Mika, Zichron Yaakov (IL); Benny Rousso, Rishen Lezion (IL); Bella Felzen, Haifa (IL); Andre Routh, Lake Jackson, TX (US)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/980,748

(22) PCT Filed: May 25, 2000

(86) PCT No.: PCT/IL00/00302
§ 371 (c)(1),
(2), (4) Date: Apr. 11, 2002

(87) PCT Pub. No.: WO00/72918
PCT Pub. Date: Dec. 7, 2000

Related U.S. Application Data

(60) Provisional application No. 60/136,092, filed on May 26, 1999.

(51) Int. Cl.
*A61N 1/00* (2006.01)
(52) U.S. Cl. ............................................. 607/5
(58) Field of Classification Search ................... 607/4, 5, 607/14
See application file for complete search history.

(56) References Cited

U.S. PATENT DOCUMENTS

| 3,211,154 | A |   | 10/1965 | Becker et al. |
| 4,554,922 | A | * | 11/1985 | Prystowsky et al. ............ 607/14 |
| 4,559,946 | A |   | 12/1985 | Mower |
| 4,637,397 | A |   | 1/1987  | Jones et al. |
| 4,693,253 | A |   | 9/1987  | Adams |
| 4,708,145 | A |   | 11/1987 | Tacker, Jr. et al. |
| 4,996,984 | A |   | 3/1991  | Sweeney |
| 4,998,531 | A |   | 3/1991  | Bocchi et al. |
| 5,048,522 | A |   | 9/1991  | Petrofsky |
| 5,063,929 | A |   | 11/1991 | Bartlet et al. |
| 5,107,834 | A |   | 4/1992  | Ideker et al. |
| 5,111,814 | A |   | 5/1992  | Goldfarb |
| 5,163,427 | A |   | 11/1992 | Keimel |

(Continued)

FOREIGN PATENT DOCUMENTS

WO  WO 96/16696  6/1996

(Continued)

OTHER PUBLICATIONS

USPTO Office Action dated Sep. 29, 2010 for U.S. Appl. No. 11/933,168.

*Primary Examiner* — Niketa I Patel
*Assistant Examiner* — Rex Holmes
(74) *Attorney, Agent, or Firm* — William H. Dippert; Eckert Seamans Cherin & Mellott, LLC

(57) ABSTRACT

Apparatus (18) is provided for defibrillating a heart (20) of a person. The apparatus (18) includes one or more electrodes (100) that are adapted to be coupled to the heart, and a control unit (90) that is adapted to drive the electrodes to apply electrical pulses to the heart at a rate which is typically greater than about 10 Hz. The control unit terminates the electrical pulses, so that the heart beats without fibrillation. Other embodiments are also described.

13 Claims, 10 Drawing Sheets

U.S. PATENT DOCUMENTS

| | | | |
|---|---|---|---|
| 5,184,616 A | 2/1993 | Weiss | |
| 5,318,591 A | 6/1994 | Causey et al. | |
| 5,325,856 A | 7/1994 | Nitzsche et al. | |
| 5,366,485 A | 11/1994 | Kroll et al. | |
| 5,431,682 A | 7/1995 | Hedberg | |
| 5,431,688 A | 7/1995 | Freeman | |
| 5,447,525 A | 9/1995 | Powell et al. | |
| 5,464,429 A | 11/1995 | Hedberg et al. | |
| 5,472,453 A | 12/1995 | Alt | |
| 5,489,293 A * | 2/1996 | Pless et al. | 607/5 |
| 5,522,853 A | 6/1996 | Kroll | |
| 5,527,345 A | 6/1996 | Infinger | |
| 5,620,468 A | 4/1997 | Mongeon et al. | |
| 5,674,251 A | 10/1997 | Combs et al. | |
| 5,683,429 A * | 11/1997 | Mehra | 607/14 |
| 5,697,953 A | 12/1997 | Kroll et al. | |
| 5,713,924 A * | 2/1998 | Min et al. | 607/4 |
| 5,713,929 A * | 2/1998 | Hess et al. | 607/14 |
| 5,797,967 A | 8/1998 | KenKnight | |
| 2002/0123771 A1 * | 9/2002 | Ideker et al. | 607/14 |

FOREIGN PATENT DOCUMENTS

| | | |
|---|---|---|
| WO | WO 98/10830 | 3/1998 |
| WO | WO 98/19719 | 4/1998 |

* cited by examiner

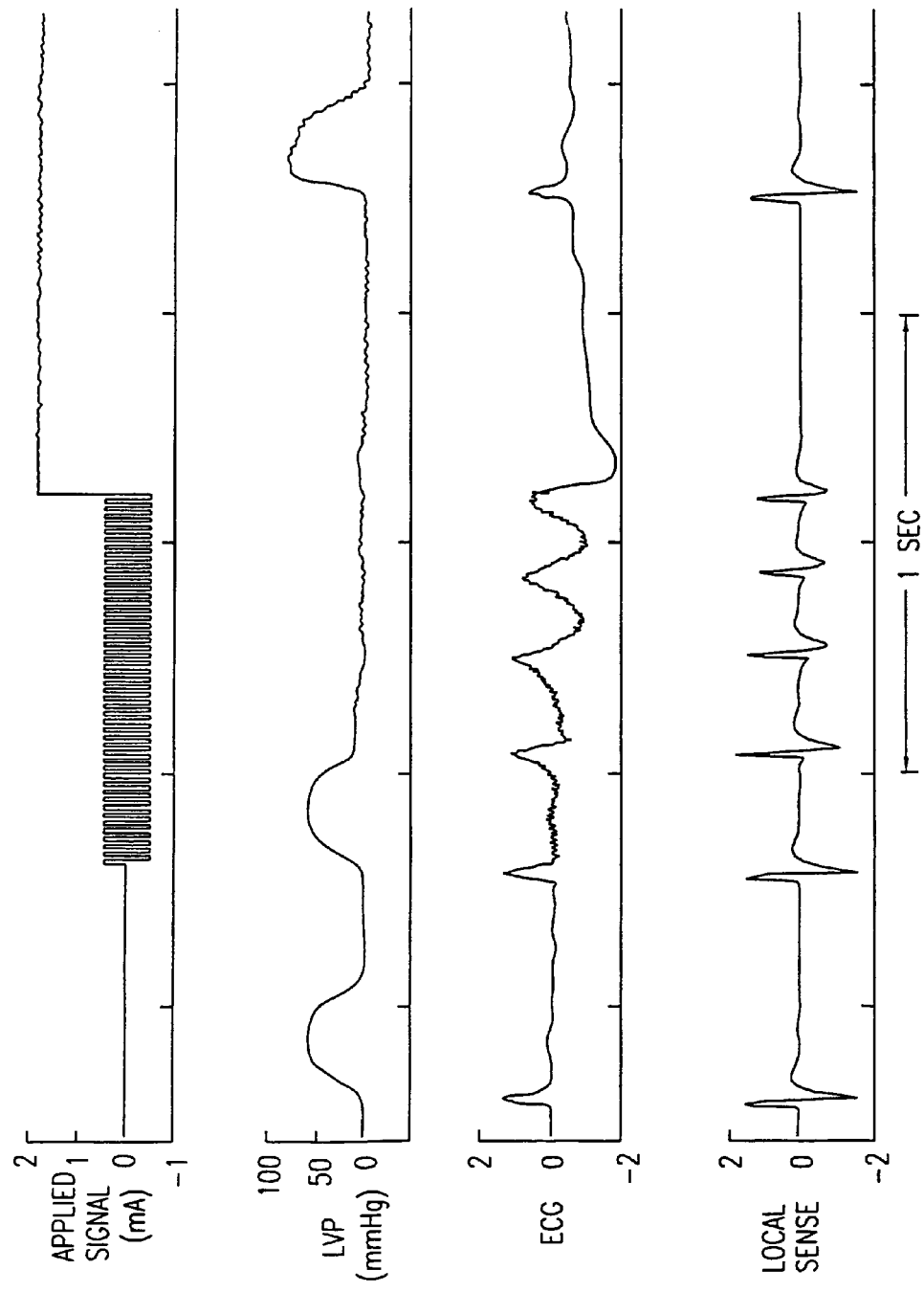

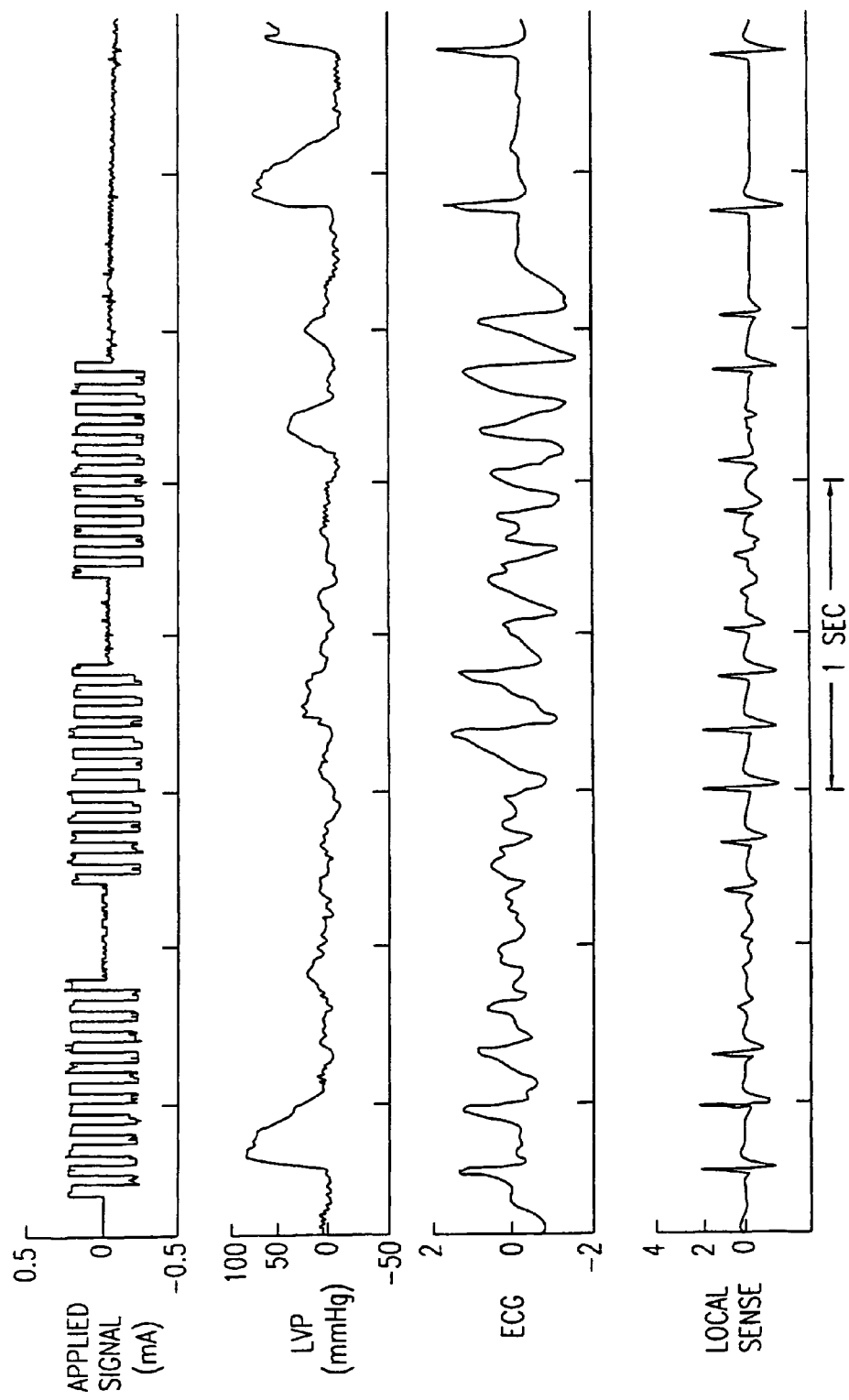

SHOCKLESS DEFIBRILLATION

CROSS-REFERENCE TO RELATED APPLICATIONS

This application claims the benefit of U.S. Provisional Patent Application 60/136,092, entitled "Shockless defibrillation," filed May 26, 1999, which is assigned to the assignee of the present patent application and is incorporated herein by reference.

FIELD OF THE INVENTION

The present invention relates generally to devices and methods for treatment of the heart, and specifically to devices and methods for treating cardiac arrhythmias.

BACKGROUND OF THE INVENTION

Implantable cardioverter-defibrillators (ICDs) and other invasive anti-arrhythmic devices are well known in the art. A typical ICD includes a sensing circuit, which detects the onset of fibrillation or other potentially dangerous arrhythmic activity. When fibrillation is detected, the ICD applies a short, high-intensity electrical shock to electrodes in or on the heart, causing current to flow through the heart. The shock typically delivers about 10 joules of energy. The object of the shock is to terminate temporarily all cardiac activity, following which rhythmic activity of the heart resumes, either spontaneously or due to application of pacing pulses. In a conscious patient, the shock of defibrillation is very painful. It is noted that if a high level of the applied energy is concentrated in a relatively small region of the heart, then transient or permanent injury may be caused to the affected region.

Cardioversion, in which a shock of much lower intensity is applied to the heart, may also be used to interrupt arrhythmic activity. The cardioversion pulse attempts to interrupt arrhythmia by correcting the synchronization of contraction of different parts of the heart muscle. Cardioversion can be useful in terminating atrial fibrillation or ventricular tachycardia, but it is generally not effective in controlling the more serious condition of ventricular fibrillation.

U.S. Pat. Nos. 5,797,967 to KenKnight and 5,472,453 to Alt, which are incorporated herein by reference, describe methods and apparatus for applying electrical energy to the heart so as to treat arrhythmias.

SUMMARY OF THE INVENTION

It is an object of some aspects of the present invention to provide methods and apparatus for shockless defibrillation of the heart.

In preferred embodiments of the present invention, an electrical shockless defibrillator comprises two or more electrodes, placed at multiple sites in or on the body of a patient, and an electrical control unit. When it is determined that fibrillation or other dangerous arrhythmic activity is occurring in the heart, the control unit administers a signal comprising one or more pulses to at least one of the electrodes, typically reducing or substantially stopping activity of the heart for the duration of pulse application. Stopping heart activity in this way interrupts the arrhythmic activity and/or fibrillation. Termination of signal application then allows the heart to resume normal beating in a synchronized state.

In some preferred embodiments of the present invention, the defibrillator is implanted in the patient's body, and the electrodes are placed in or on the patient's heart. Alternatively or additionally, one of the electrodes is placed in or on the heart, and another electrode, typically comprising a metal case of the control unit, is placed in or on the patient's body. Alternatively, the defibrillator is not implanted, and the signal is administered through electrodes typically placed on the patient's chest.

Preferably, the signal comprises a sequence of rapid pulses, applied through one or more of the electrodes. The rapid pulses typically have a magnitude and duration similar to standard pacing pulses, and induce a state of generally-constant contraction of most or substantially all of the heart muscle. This state, which some readers may interpret as tetany (i.e., sustained muscular contraction induced by rapid stimulation) is produced, in a preferred embodiment, by applying through a plurality of electrodes a 5-30 Hz signal to the heart. While in the state of contraction, the cells of the heart tissue are not generally susceptible to propagation of action potentials therethrough, so that reentrant circuits in the tissue associated with fibrillation and other arrhythmic activity cannot operate.

It is noted that the signal may comprise combinations of the different forms of electrical energy described herein, and that parameters of the signal may change while it is being applied. For example, the pulses may be applied initially at a high frequency (e.g., 30 Hz), then reduced during application to a low, final frequency, which may even be as low as normal sinus rhythm.

Because the mechanism of defibrillation used by the shockless defibrillator in accordance with preferred embodiments of the present invention is substantively different from conventional defibrillation, the signal that it applies is preferably of substantially lower amplitude and of greater duration than defibrillation pulses known in the art. Preferably, the shockless defibrillation signal has a duration of at least 100 milliseconds, most preferably about 1-2 seconds, and delivers about 1 joule of energy or less.

In some preferred embodiments of the present invention, termination of the shockless defibrillation signal is followed by the application of normal pacing pulses to one or more of the electrodes, so as to restore the heart to normal beating. In other preferred embodiments, the heart automatically resumes normal sinus rhythm after termination of the shockless defibrillation signal, and there is no need for such pacing pulses.

In some preferred embodiments of the present invention, at least some of the electrodes are placed at multiple sites on the epicardium and/or endocardium of the left and right ventricles. Typically, each electrode coupled to the control unit conveys a particular waveform to the heart, which may differ in certain aspects from the waveforms applied to other electrodes. The particular waveform is preferably determined by the unit under the control or supervision of a human operator during an initial calibration period when the electrodes are implanted. Aspects of the waveforms which can be set typically include, but are not limited to, parameters such as time shifts between application of signals at different electrodes, signal shapes, amplitudes, DC offsets, pulse durations, frequencies and duty cycles.

In some preferred embodiments of the present invention, a "fencing" signal is applied at one or more locations in or on the heart, in order to inhibit an action potential from developing, and/or to prevent an action potential from propagating from one region of the heart to another. Such fencing is described in PCT Patent Publication WO98/10830, which entered the US national phase as U.S. patent application Ser. No. 09/254,903, entitled "Fencing of cardiac muscles," which are both assigned to the assignee of the present patent application and incorporated herein by reference. The fencing signal generally produces several "blocking regions" on the myocardium, which divide the myocardium into volumes which are too small to support fibrillation or reentrant circuits.

In some preferred embodiments of the present invention, one or more motion sensors, e.g., accelerometers, are coupled to or disposed near the heart, and send signals to the control unit indicative of cardiac motion. The motion signals serve as feedback, to enable the control unit to determine when fibrillation is occurring, whereupon the shockless defibrillation signal is applied. Additionally, the motion signals may be used to verify that the heart has returned to normal beating after defibrillation. Feedback from the motion sensors is believed to be particularly beneficial because restoration of normal cardiac electrical signals is not necessarily associated with completely-restored cardiac function (i.e., the heart may be in a state of electro-mechanical dissociation). Moreover, while electrical signals are being applied to the heart, it may be difficult to accurately assess the electrical activity of the heart.

Alternatively or additionally, one or more sensors, which generate signals indicative of, for example, local electrical activity and/or Left Ventricular Pressure (LVP), monitor the heart's behavior to detect an abnormal, potentially-dangerous condition, such as fibrillation or other arrhythmia. Algorithms and/or circuitry associated with the control unit which detect the condition preferably initiate defibrillation or other appropriate therapy responsive to the sensor signals. The sensors are preferably also used in monitoring recovery of normal beating of the heart following defibrillation.

In a preferred embodiment, application of the electrical stimuli defibrillates the heart within a very short period, typically about 1 second. The heart generally returns to normal function within about 2 seconds of removal of the electrical stimuli, typically during a period of standard pacing following defibrillation.

There is therefore provided, in accordance with a preferred embodiment of the present invention, a method for defibrillating a heart of a person, including:
applying electrical pulses to the heart at a rate greater than about 10 Hz; and
terminating the electrical pulses, so that the heart beats without fibrillation.

Preferably, applying the pulses includes applying the pulses for at least about 100 milliseconds.

Alternatively or additionally, applying the pulses includes applying to the heart a total amount of electrical energy which is less than about 1 joule.

Further alternatively or additionally, applying the pulses includes applying a pulse having an amplitude less than about 50 mA.

In a preferred embodiment, the method includes sensing motion of the heart, and applying the pulses includes modifying a characteristic of at least some of the pulses applied to the heart responsive to the sensed motion.

In a preferred embodiment, the method includes applying a fencing signal to the heart to inhibit propagation of an activation wave therein while applying the electrical pulses.

In a preferred embodiment, applying the pulses includes applying the pulses in two or more bursts of pulses.

Preferably, the method includes pacing the heart at approximately 1 Hz while applying the electrical pulses at the rate greater than about 10 Hz.

Further preferably, applying the pulses includes applying electrical energy to the heart at a peak rate which is less than about 100 W. Still further preferably, applying the pulses includes applying electrical energy to the heart at a peak rate which is less than about 10 W.

Typically, applying the pulses includes applying respective signals at a plurality of sites on the heart. Optionally, applying the signals includes applying a first waveform at a first one of the sites and applying a second waveform, which differs from the first waveform, at a second one of the sites.

Preferably, applying the pulses includes applying the pulses so as to induce depolarization in at least a region of the heart. Further preferably, applying the pulses includes applying the pulses so as to induce a depolarization of substantially all excitable contractile tissue of the heart. Still further preferably, applying the pulses includes applying the pulses so as to induce a substantially sustained contraction of the region lasting at least about 250 milliseconds.

There is further provided, in accordance with a preferred embodiment of the present invention, a method for defibrillating a heart of a person, including:
applying an electrical signal to the heart for at least 100 milliseconds; and
terminating the electrical signal, so that the heart beats without fibrillation.

There is still further provided, in accordance with a preferred embodiment of the present invention, a method for defibrillating a heart of a person, including:
applying an electrical signal to the heart with a total energy of no more than about 1 joule; and
terminating the electrical signal, so that the heart beats without fibrillation.

Preferably, applying the electrical signal includes modifying a parameter of the signal during the application thereof. Alternatively or additionally, applying the signal includes applying to the heart electrical pulses at a first frequency, and terminating the electrical signal includes reducing the frequency to a second frequency.

There is yet further provided, in accordance with a preferred embodiment of the present invention, apparatus for defibrillating a heart of a person, including:
one or more electrodes, adapted to be coupled to the heart; and
a control unit, adapted to drive the electrodes to apply electrical pulses to the heart at a rate greater than about 10 Hz, and to terminate the electrical pulses, so that the heart beats without fibrillation.

Preferably, the apparatus includes a sensor, adapted to sense motion of the heart and to convey a sensor signal responsive thereto to the control unit. The control unit is preferably adapted to modify a characteristic of at least some of the pulses applied to the heart responsive to the sensor signal.

In a preferred embodiment, the apparatus includes a fencing electrode, adapted to be coupled to the heart. Preferably, the control unit drives the fencing electrode to apply a fencing signal to the heart to inhibit propagation of an activation wave therein, while concurrently driving the one or more electrodes to apply the electrical pulses.

Alternatively or additionally, the apparatus includes a pacing electrode, adapted to be coupled to the heart. Preferably, the control unit is adapted to drive the pacing electrode to pace the heart at approximately 1 Hz, while concurrently driving the one or more electrodes to apply the electrical pulses. Optionally, the one or more electrodes include first and second electrodes, and the control unit is adapted to drive the first electrode to apply a first waveform at a first site of the heart, and is adapted to drive the second electrode to apply a second waveform, which differs from the first waveform, at a second site of the heart.

There is also provided, in accordance with a preferred embodiment of the present invention, apparatus for defibrillating a heart of a person, including:

one or more electrodes, adapted to be coupled to the heart; and a control unit, adapted to drive the electrodes to apply an electrical signal to the heart for at least 100 milliseconds, and to terminate the electrical signal, so that the heart beats without fibrillation.

There is further provided, in accordance with a preferred embodiment of the present invention, apparatus for defibrillating a heart of a person, including:

one or more electrodes, adapted to be coupled to the heart; and a control unit, adapted to drive the electrodes to apply an electrical signal to the heart with a total energy of no more than about 1 joule, and to terminate the electrical signal, so that the heart beats without fibrillation.

The present invention will be more fully understood from the following detailed description of the preferred embodiments thereof, taken together with the drawings, in which:

BRIEF DESCRIPTION OF THE DRAWINGS

FIG. 10 schematically illustrates electrical signals applied to a beating pig heart; in accordance with a preferred embodiment of the present invention, and experimental results obtained thereby; and FIG. 11 schematically illustrates electrical signals applied to a beating pig heart, in accordance with a preferred embodiment of the present invention, and experimental results obtained thereby.

DETAILED DESCRIPTION OF PREFERRED EMBODIMENTS

Figure 1:
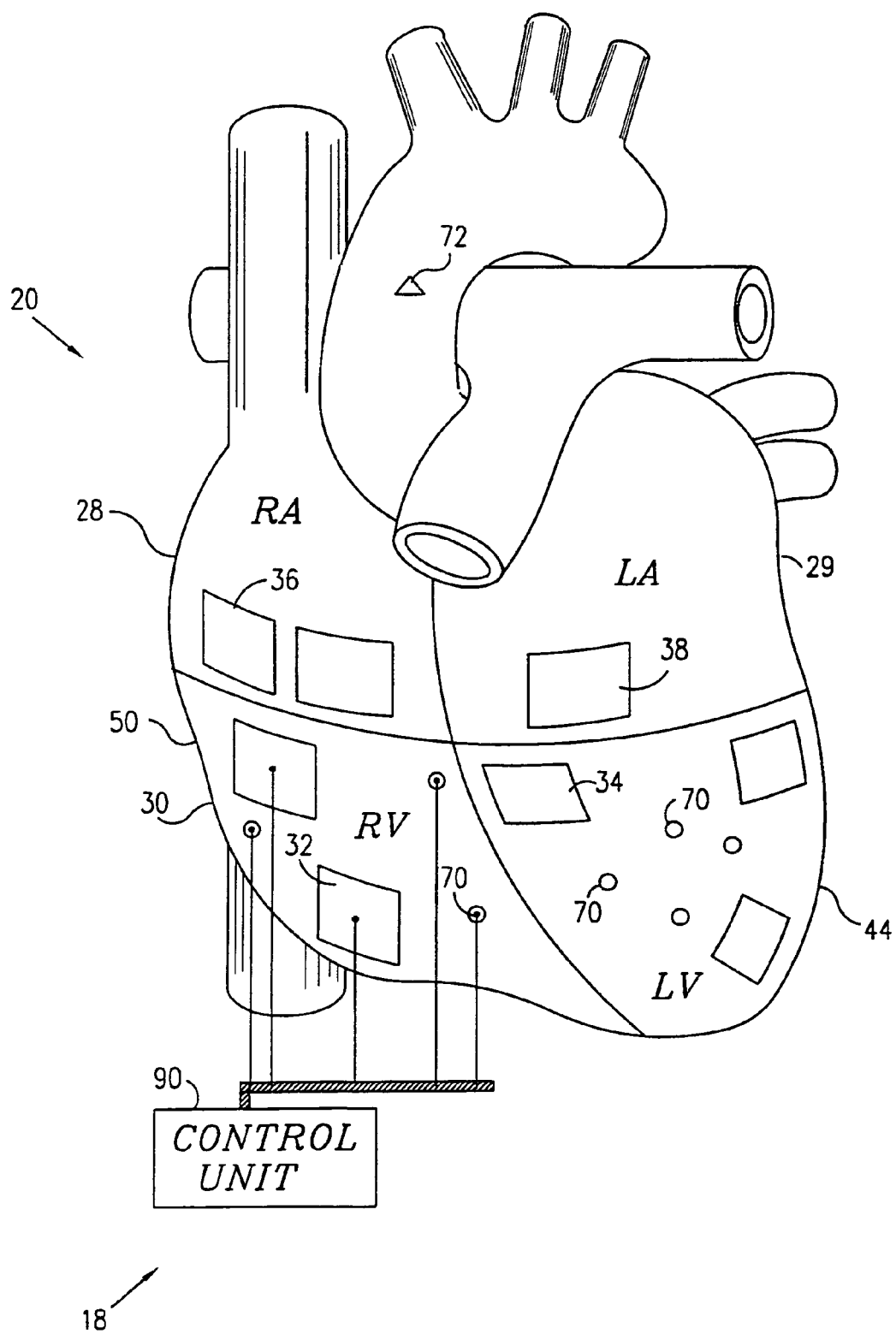
FIG. 1 is a schematic illustration of the external surface of a heart, showing the placement of patch electrodes thereon, in accordance with a preferred embodiment of the present invention.

FIG. 1 is a schematic illustration of apparatus 18 for defibrillating a patient's heart 20, in accordance with a preferred embodiment of the present invention. One or more patch electrodes 32, 34, 36, and 38, are coupled to the epicardium 50 overlying, respectively, the right and left ventricles 30 and 44 and right and left atria 28 and 29. Additionally, optional motion sensors 70 (e.g., accelerometers) and one or more optional supplemental sensors 72 are coupled to the heart or placed elsewhere on or in the patient's body. A control unit 90, preferably coupled to all of the electrodes and sensors, is used to control heart activity, and specifically to defibrillate the heart, as described hereinbelow. Preferably, control unit 90 is implanted in the patient's body, as is known in the art of pacemakers and ICDs. Alternatively, the control unit may be an external unit. For clarity, connections between control unit 90 and only some of the electrodes and sensors are shown in FIG. 1.

In a preferred embodiment, motion sensors 70 and supplemental sensors 72 comprise one or more of the following:

a Left Ventricular Pressure (LVP) and/or d(LVP)/dt sensor,
a systemic blood pressure sensor,
an electrocardiographic (ECG) sensor,
blood gas sensors, such as $pCO_2$, $pO_2$, $SvO_2$ sensors,
blood flow rate sensors,
heart wall motion sensors, optionally based on accelerometers, strain gauges, ultrasonic sensors, or magnetic sensors,
chamber volume sensors, and
intramyocardial pressure sensors.

Figure 2:
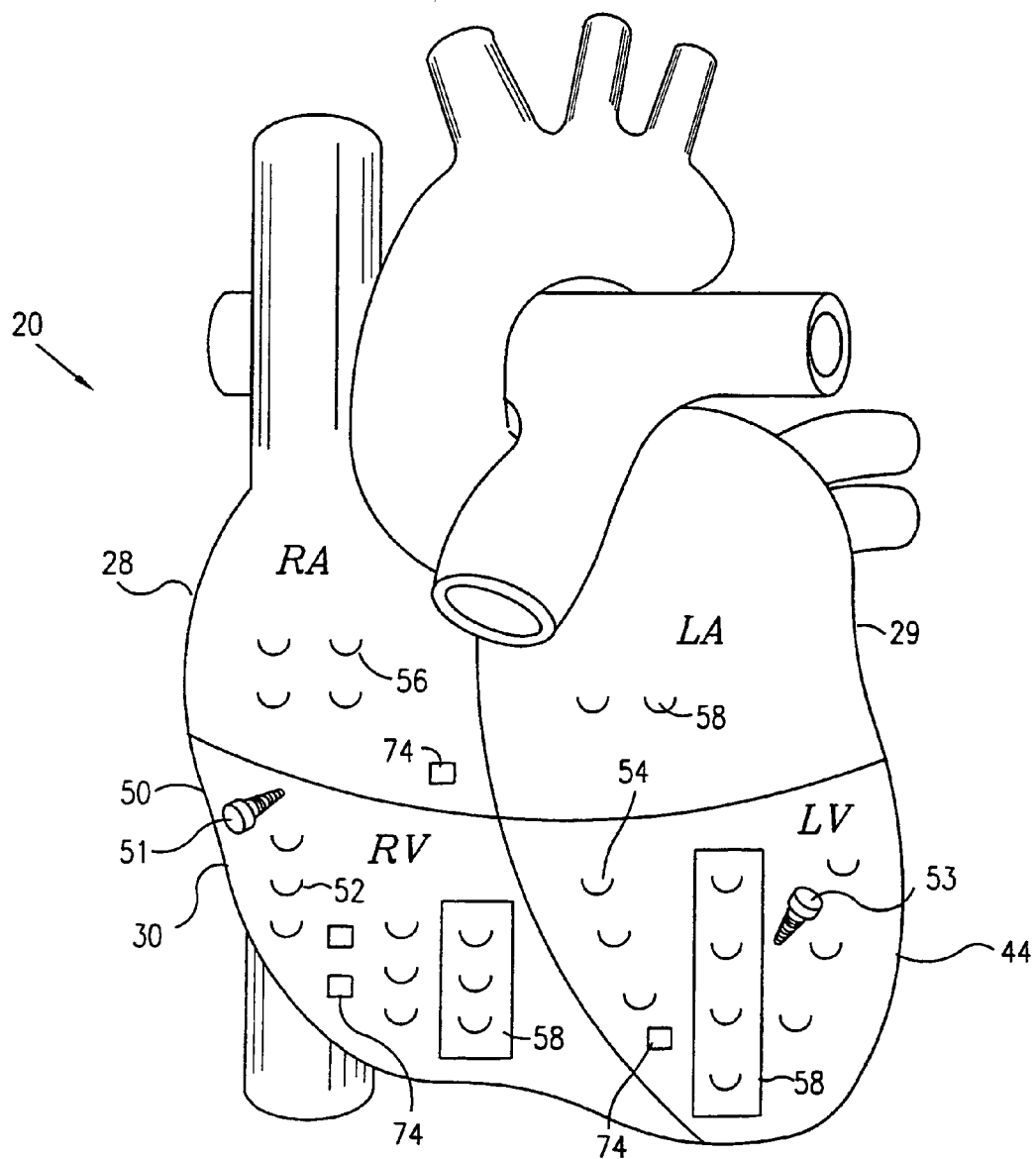
FIG. 2 is a schematic illustration of the external surface of a heart, showing the placement of needle and screw electrodes thereon, in accordance with a preferred embodiment of the present invention.

FIG. 2 is a schematic illustration showing the placement of one or more screw electrodes 51 and 53 and needle and/or wire electrodes 52, 54, and 56 onto epicardium 50, in accordance with a preferred embodiment of the present invention. Preferably, the electrodes shown in FIG. 2 are coupled to control unit 90 (not shown). Some of the needle and/or wire electrodes are optionally coupled to strips 58, which are themselves coupled to heart 20, in order to improve the coupling between the electrodes and the heart and to increase ease of use. Local sense electrodes 74, are preferably coupled to the epicardium or placed within one or more chambers of the heart, and convey electrical signals responsive to cardiac electric activity to circuitry described hereinbelow with reference to FIG. 5. Alternatively or additionally, the screw, needle, or wire electrodes may be used for local sensing, as well as stimulation.

Figure 3:
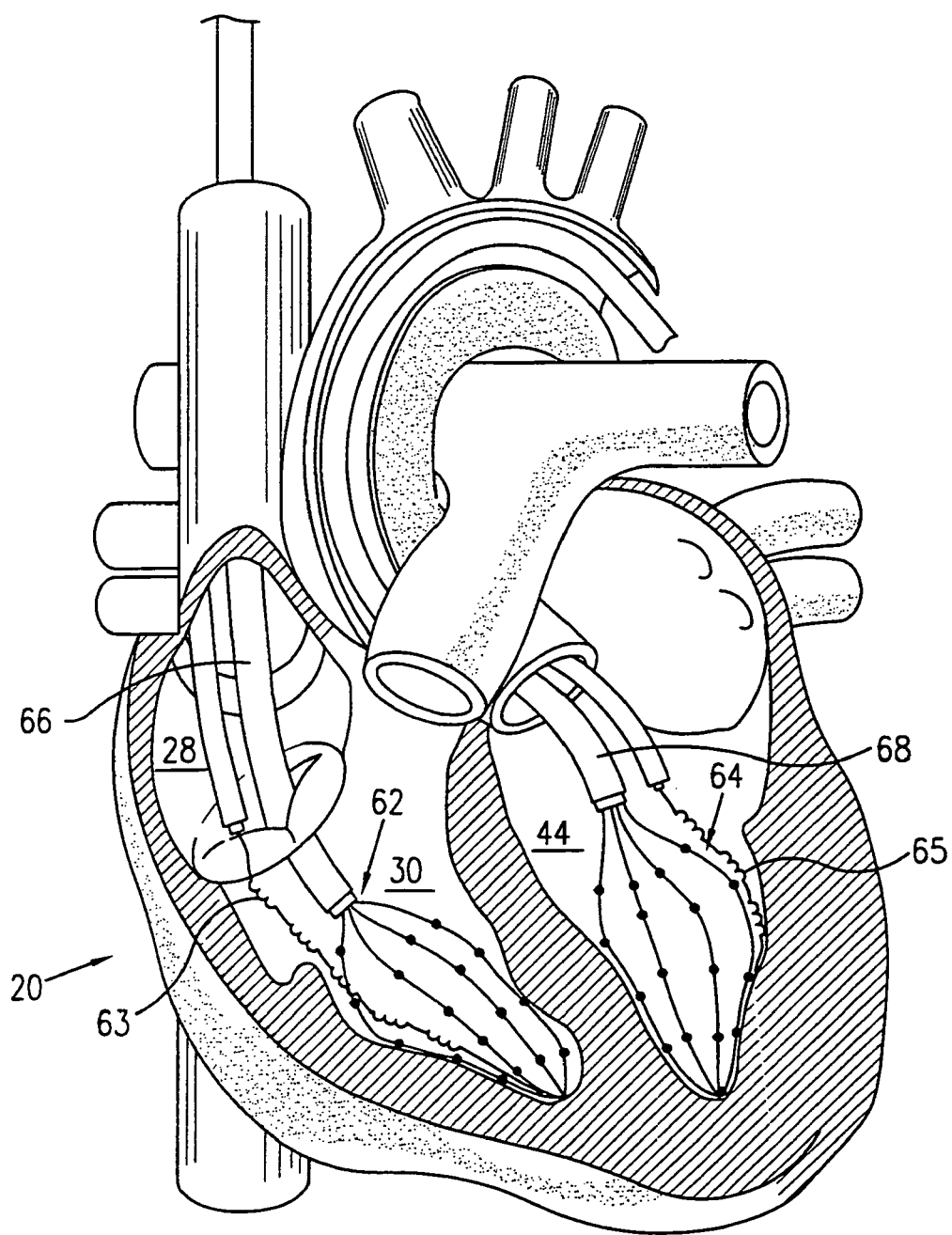
FIG. 3 is a schematic, sectional illustration of a heart, showing the placement of endocardial basket electrodes, coil electrodes, and defibrillation electrodes, in accordance with a preferred embodiment of the present invention.

FIG. 3 is a schematic, sectional illustration of heart 20, showing the placement of endocardial basket electrodes 62 and 64, and defibrillation and/or coil electrodes 63 and 65, in accordance with a preferred embodiment of the present invention. Preferably, the electrodes shown in FIG. 3 are coupled to control unit 90 (not shown). Catheters 66 and 68 preferably pass basket electrodes 62 and 64 through the vena cava and aorta, respectively, and subsequently actuate basket electrodes to open in the ventricles. Electrodes 63 and 65 are preferably positioned in their respective locations in a similar manner. In general, the electrode configuration shown in FIG. 3 is suitable for testing purposes, or for in-hospital patients, who may already have had catheters with suitable electrodes inserted into their hearts.

Figure 4:
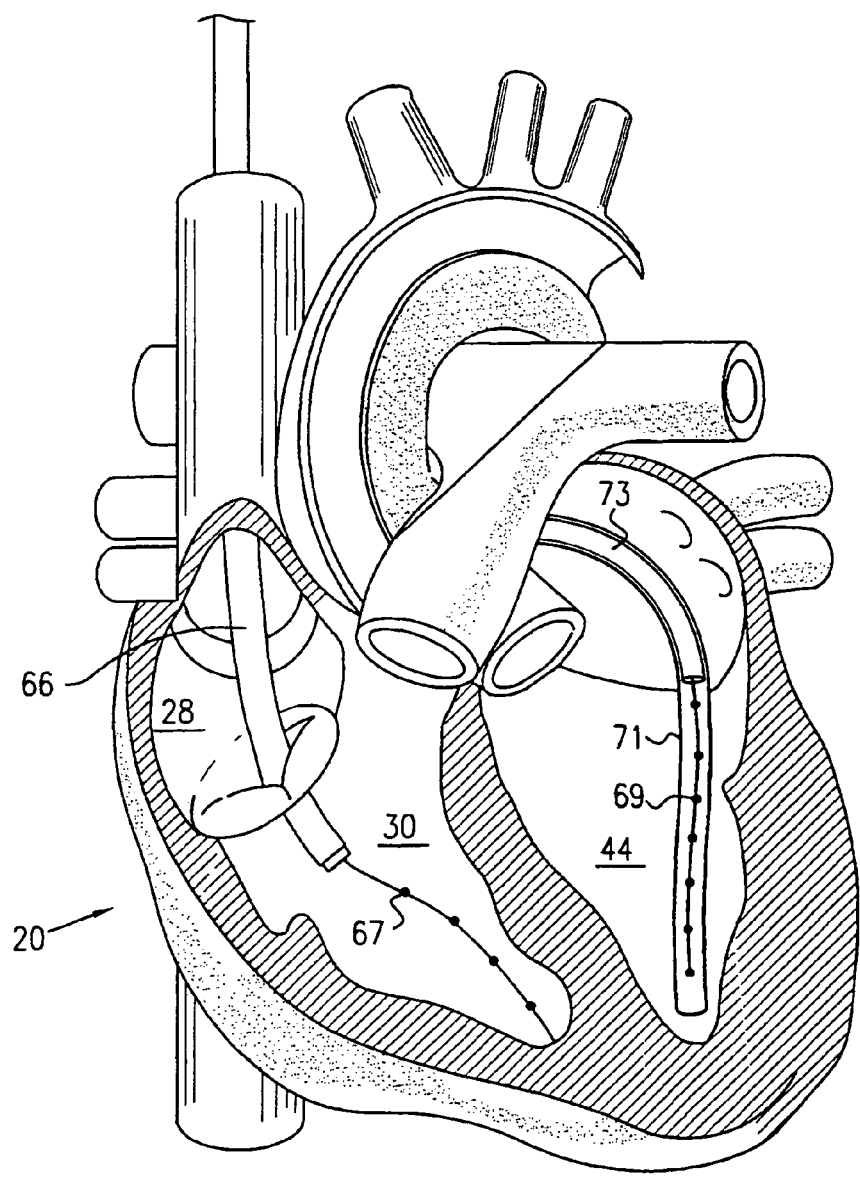
FIG. 4 is a schematic, sectional illustration of a heart, showing the placement of transvascular electrodes therein, in accordance with another preferred embodiment of the present invention.

FIG. 4 is a schematic, sectional illustration of heart 20, showing the placement by catheter 66 of electrodes 67 into right ventricle 30, and the placement of other electrodes 69 by a catheter 73 into the great cardiac vein 71, in accordance with a preferred embodiment of the present invention. In a typical application, control unit 90 (not shown) is implanted in the right pectoral region, and drives a defibrillating current between two or more of the various electrodes, and/or between one or more of the electrodes and a metal case of the control unit. In a preferred embodiment, at least some of electrodes 67 and 69 comprise coil electrodes.

It will be understood by one skilled in the art that the types and placement of electrodes in FIGS. 1-4 are shown by way of example. Other sites in and around the heart are appropriate for electrode or sensor placement in other applications of the present invention. Additionally, different numbers of electrodes or sensors (including no electrodes or sensors in some areas) and different types and combinations of the above-cited sensors and electrodes, or other types of electrodes or sensors, may be used in applying the principles of the present invention.

Figure 5:
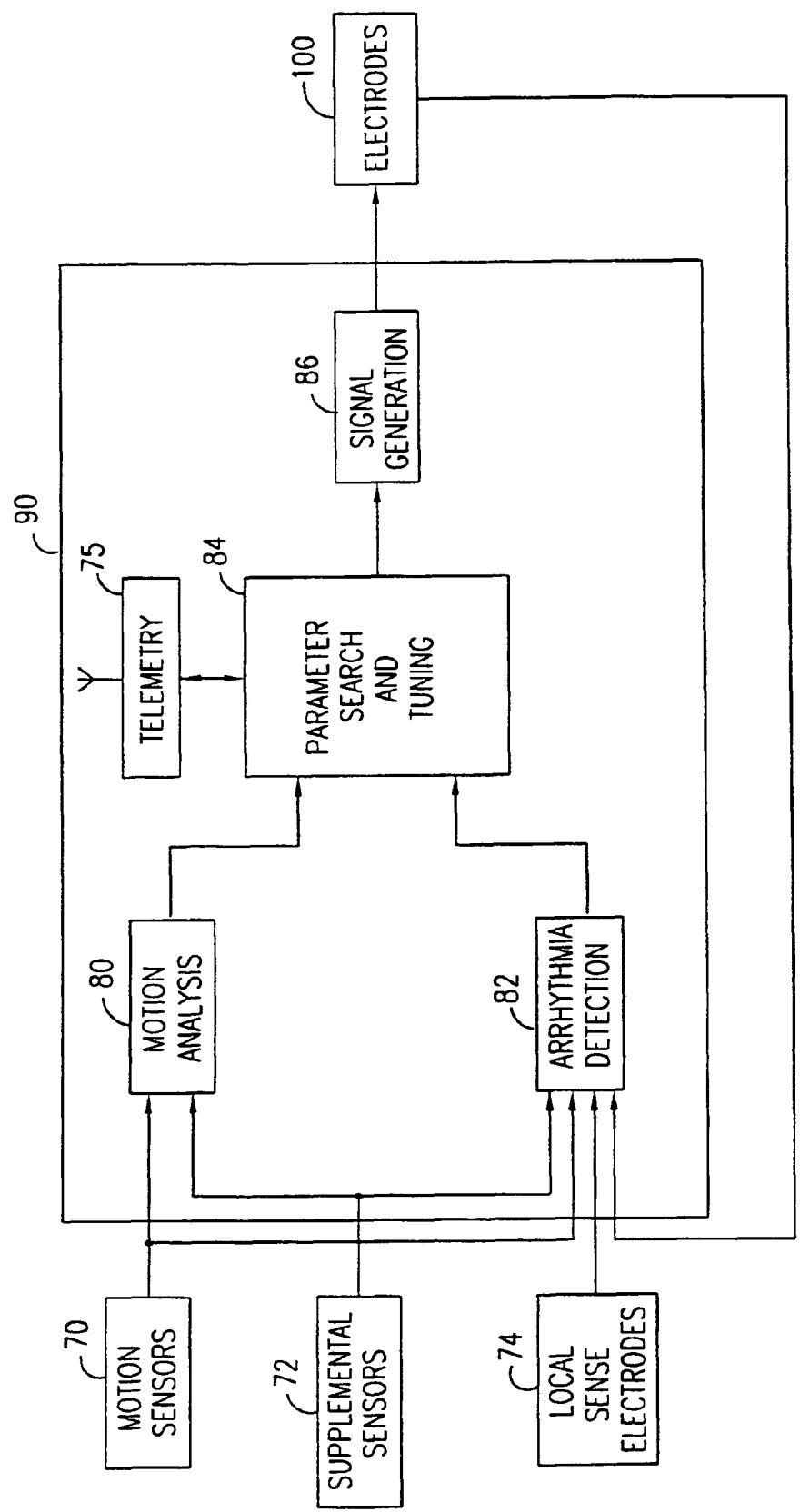
FIG. 5 is a schematic block diagram of a control unit, which generates signals to be applied to the electrodes shown in the preceding figures, in accordance with a preferred embodiment of the present invention.

FIG. 5 is a schematic block diagram of control unit 90, which conveys electrical energy to electrodes 100 coupled to heart 20 in order to terminate arrhythmic activity of the heart, in accordance with a preferred embodiment of the present invention. Typically, electrodes 100 comprise one or more of the electrodes shown in FIGS. 1-4, and, optionally, one or more electrodes elsewhere in or on the surface of the patient's body. Preferably, control unit 90 conveys electrical energy to one or more of electrodes 100, in order to substantially stop arrhythmic activity of heart 20, such as fibrillation, and subsequently terminates application of the energy to enable the heart to beat again. Most preferably, control unit 90 applies standard pacing pulses to the heart through one or more of the electrodes, so as to restore a normal heart beat after defibrillation. Alternatively, the heart resumes normal sinus rhythm by itself after the defibrillation, so that pacing is not necessary.

Preferably, the defibrillating electrical energy comprises rapid pulses, generally similar in form and intensity to pulses used to pace the heart, which are applied through some of electrodes 100 to heart 20. The pulses induce a reversible state of substantially-constant contraction of most or substantially all of the heart muscle. Typically, the rapid pulse application interrupts reentrant activation circuits in the heart, so that the arrhythmia cannot resume, and normal beating ensues after the rapid pulses are terminated. Preferred timing, shape, and magnitude parameters of the rapid pulses are described hereinbelow.

Alternatively or additionally, control unit 90 applies a "fencing" signal to some of electrodes 100, in order to prevent generation of an action potential, and/or to prevent the propagation of an action potential from one region of the heart to another. Suitable methods for applying the fencing signal are described in the above-cited U.S. patent application Ser. No. 09/254,903. The fencing signal generally produces several "blocking regions" on the myocardium, which divide the myocardium into volumes which are too small to support fibrillation. When the fencing signal is applied in conjunction with rapid pulses, motion of the heart either stops essentially completely, or continues only as a very fine flutter. This condition is typically spontaneously reversible upon termination of the application of the signals to the heart. Thus, the heart generally resumes normal beating without assistance. Nevertheless, standard pacing pulses at a normal heart rate are typically applied to the heart after shockless defibrillation, in order to return the heart to normal rhythm and/or to reduce the likelihood of a recurrence of the arrhythmia. In a preferred embodiment, apparatus 18 is equipped with standard defibrillation and cardioversion means, in case normal beating is not successfully resumed after shockless defibrillation.

During routine operation of apparatus 18, the heart is supposed to be pumping blood regularly. To verify proper cardiac function during these periods, an arrhythmia detection block 82 of control unit 90 preferably receives inputs from sensors 70 and 72 and from electrodes 74 and 100, performs calculations responsive to the inputs, and generates a signal responsive to detecting abnormal cardiac activity. Preferably, block 82 employs techniques known in the art for determining an onset of arrhythmia, so that control unit 90 can treat or terminate the arrhythmia by applying a low-energy, shockless defibrillation signal, as described herein. Thus, normal cardiac function is typically restored without applying the generally painful shocks associated with prior art defibrillation techniques.

As described, the heart typically exhibits a fine fluttering motion when the shockless defibrillation signal is being applied. If arrhythmia detection block 82 detects a substantial deviation from an expected motion profile or electrical activity profile, then the control unit typically modifies or terminates application of the signal and, as appropriate, initiates a different anti-arrhythmic procedure.

Motion sensors 70, preferably coupled to or disposed in a vicinity of heart 20, typically send signals to a motion analysis block 80 of control unit 90. During application of defibrillating energy to the heart, the signals provide feedback to the control unit, so as to enable the control unit to adjust some or all of the above-described electrical stimuli responsive to the motion sensor signals. Typically, but not necessarily, the control unit modifies the electrical stimuli which it delivers to the heart so as to minimize the heart's total motion for the duration of the signal application.

Sensors 70 typically comprise one or more accelerometers. For example, one of the accelerometers may include a piezoelectric crystal, which produces an electrical signal responsive to deformation. Motion analysis block 80 preferably comprises amplifiers to amplify low-level signals generated by motion sensors 70, and a signal processing unit, coupled to the amplifiers, which determines respective states of motion of the accelerometers. In some applications, motion analysis block 80 additionally receives signals from one or more of supplemental sensors 72, particularly those sensors that detect mechanical phenomena such as blood flow rate and blood pressure.

Preferably, motion analysis block 80 conveys results of its motion analysis to a "parameter search and tuning" block 84 of control unit 90, which, in a preferred embodiment, iteratively modifies characteristics of the rapid pulses and/or the fencing signal so as to reduce motion signals and/or other signals indicative of continued arrhythmia. To achieve this goal, block 84 typically utilizes multivariate optimization and control methods known in the art (e.g., downhill simplex or linear state variable feedback), in order to cause the measured motion and/or other parameters to converge to desired values. As appropriate, block 84 may be reprogrammed by an external wand (not shown), which communicates with a telemetry block 75 of the control unit.

For the purposes of some embodiments of the present invention, block 84 modifies a set of controllable parameters so as to transiently minimize the aggregate motion of the heart. Preferably, the controllable parameters are conveyed by block 84 to a signal generation block 86 of control unit 90, which generates, responsive to the parameters, electrical signals that are applied by electrodes 100 to the various sites on and in heart 20. Typically, but not necessarily, block 86 generates a combination of rapid pulses and a fencing signal, as described herein. Preferably, block 86 comprises amplifiers and isolation elements known in the art of electrical signal conduction into a patient. Further preferably, block 86 is enabled to generate signals that are known in the art, such as normal pacing pulses, defibrillation shocks and/or cardioversion signals, in appropriate circumstances.

Figure 6:
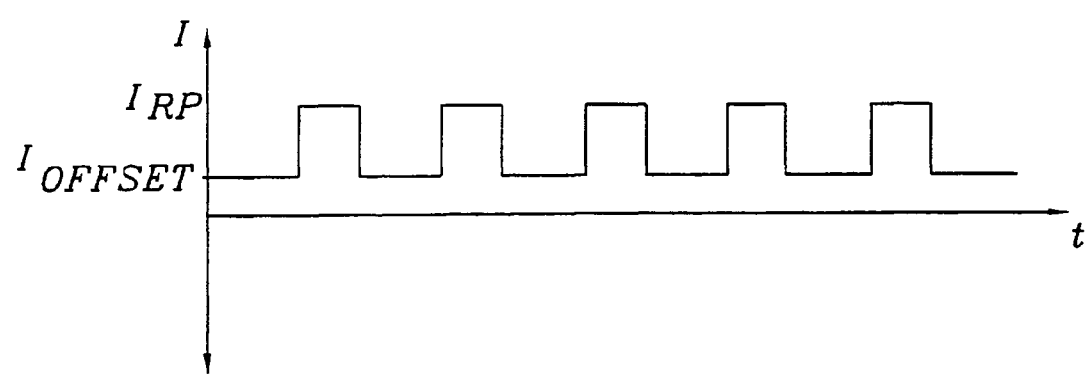
FIGS. 6, 7, and 8 are graphs schematically illustrating electrical signals generated by the control unit of FIG. 5, in accordance with respective preferred embodiments of the present invention.

FIG. 6 is a graph (not to scale) schematically illustrating pulses generated by control unit 90, and applied to heart 20 by one or more of electrodes 100, in accordance with a preferred embodiment of the present invention. In a preferred rapid pulse application mode, control unit 90 generates a regularly-spaced series of square current pulses, injecting current through the one or more electrodes into underlying cardiac tissue, in order to generate a substantially-constant contraction of the heart muscle. In this mode, the pulses are preferably characterized by a frequency above 5 Hz, and are typically applied above 10 Hz. Pulses applied between about 25 and 30 Hz have been found by the inventors to produce generally desirable results. Experiments on pigs have produced suitable results using application frequencies between about 15 and 50 Hz. In an experiment on a rabbit heart, a stimulation frequency above 100 Hz was found to be satisfactory. Other parameters typically characterizing the pulses include a duty cycle between about 5 and 50%, a DC offset ($I_{OFFSET}$) between about −10 and +10 mA, and an amplitude ($I_{RP}-I_{OFFSET}$) between about −20 and +20 mA, or −30 to +30 mA under some conditions. An amplitude of between about 1 and 5 mA, applied for a period of 1-2 seconds, is typically sufficient. These values are cited by way of example, and it will be understood that higher or lower frequencies, amplitudes and durations may also be used, depending on the type and placement of the electrodes and on the specific condition of the patient's heart.

Typically, although not necessarily, each one of electrodes 100 conveys a particular waveform to heart 20, differing in certain aspects from the waveforms applied to the other electrodes. Aspects of the waveforms which are set by the control unit and which may differ from electrode to electrode typically include parameters such as time shifts between application of waveforms at different electrodes, waveform shapes, amplitudes, DC offsets, durations, frequencies, duty cycles, shapes of rising and falling edges of pulses, and gradual changes in amplitude or other parameters over multiple pulses. For example, although FIG. 6 shows the rapid pulses as a series of monophasic pulses, it is to be understood that other waveforms, such as a sinusoid, a series of biphasic square waves, or substantially any shape known in the art of electrical stimulation of tissue could alternatively or additionally be applied in other applications of the present invention. In some operational modes, the voltage applied by some or all of electrodes 100 is controlled, rather than the current, as described hereinabove and shown in FIG. 6. Generally, the shape, magnitude, and timing of the rapid pulses are optimized for each patient at the time of implantation, using optimization algorithms known in the art, in order to store in the control unit parameters which may later be used to defibrillate the heart.

Preferably, application of the electrical stimuli in accordance with these embodiments of the present invention achieves substantially global capture of the heart within a very short period, typically about 1 second, thereby terminating the fibrillation or other arrhythmic activity. The heart typically returns to normal function within about 2 seconds of removal of the electrical stimuli.

Figure 7:
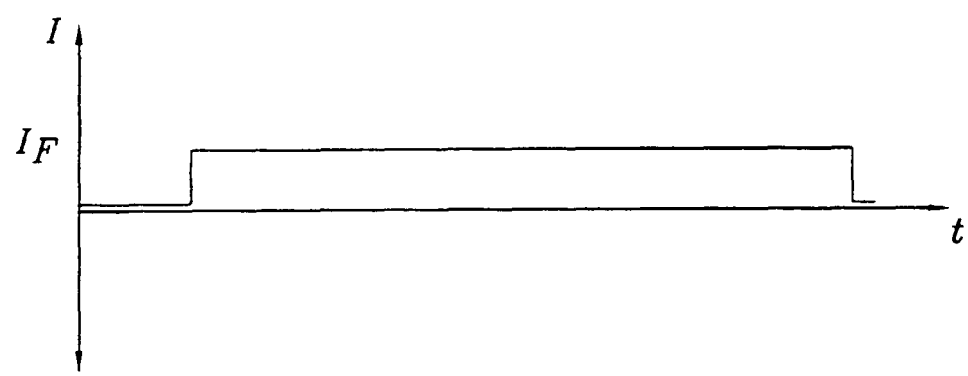

FIG. 7 is a graph schematically illustrating a fencing signal applied by a subset of electrodes 100 to respective sites on heart 20, in accordance with a preferred embodiment of the present invention. Preferably, the fencing signal is applied at the same time as the application of rapid pulses by a second subset of electrodes 100. Typically, the magnitude of the fencing signal is between about −10 mA and +10 mA, although for some applications of the present invention, other values are appropriate. Additionally, although FIG. 7 shows the fencing signal as being DC, in some operational modes, the magnitude of the fencing signal may vary.

In some applications, standard pacing signals, delivered by one or more of electrodes 100 and/or by a previously-implanted pacemaker, are applied both during routine operation and during application of signals provided by these embodiments of the present invention. In these applications, the standard pacing signals are believed to help the heart maintain order in regions thereof which are not directly affected by the shockless defibrillation signals. It is additionally believed that continued application of the standard pacing signals may help improve an aspect of the heart's recovery after fibrillation, e.g., by decreasing the time before normal beating resumes.

Figure 8:
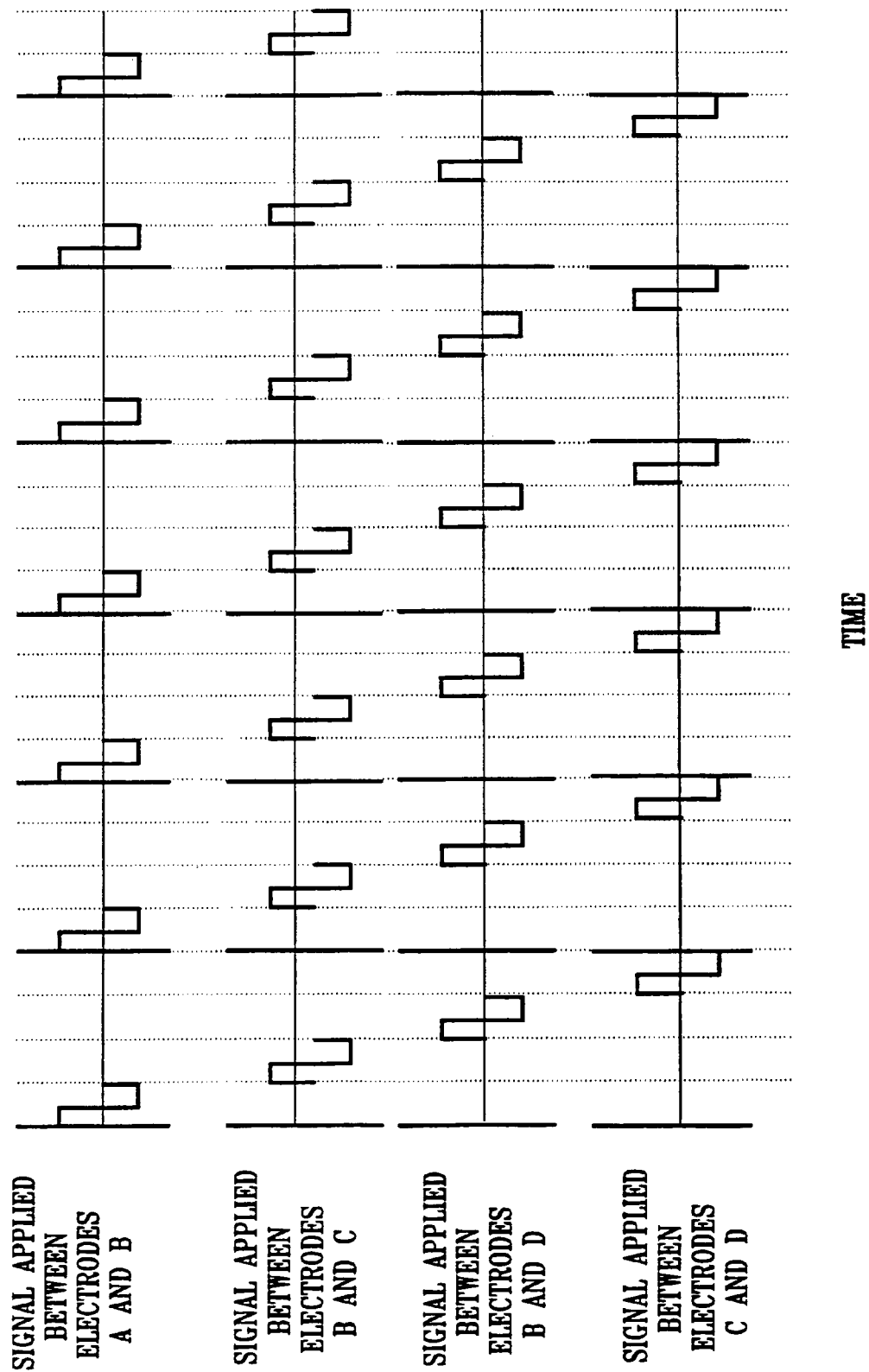

FIG. 8 is a graph schematically illustrating a set of signals applied to the heart using four electrodes, A, B, C, and D, in accordance with a preferred embodiment of the present invention. Preferably, but not necessarily, electrode A comprises the case of control unit 90, and electrodes B, C, and D comprise any of the electrodes described hereinabove with reference to FIGS. 1-4.

In a preferred embodiment, electrodes B and C are placed in or near the heart by a common catheter, and electrode D is coupled to another catheter or is fixed to the heart. Preferably, control unit 90 drives the electrodes to apply fencing signals that create blocking regions on the myocardium, and actively conducts the blocking regions to a plurality of areas of the heart, so as to terminate the fibrillation.

Figure 9:
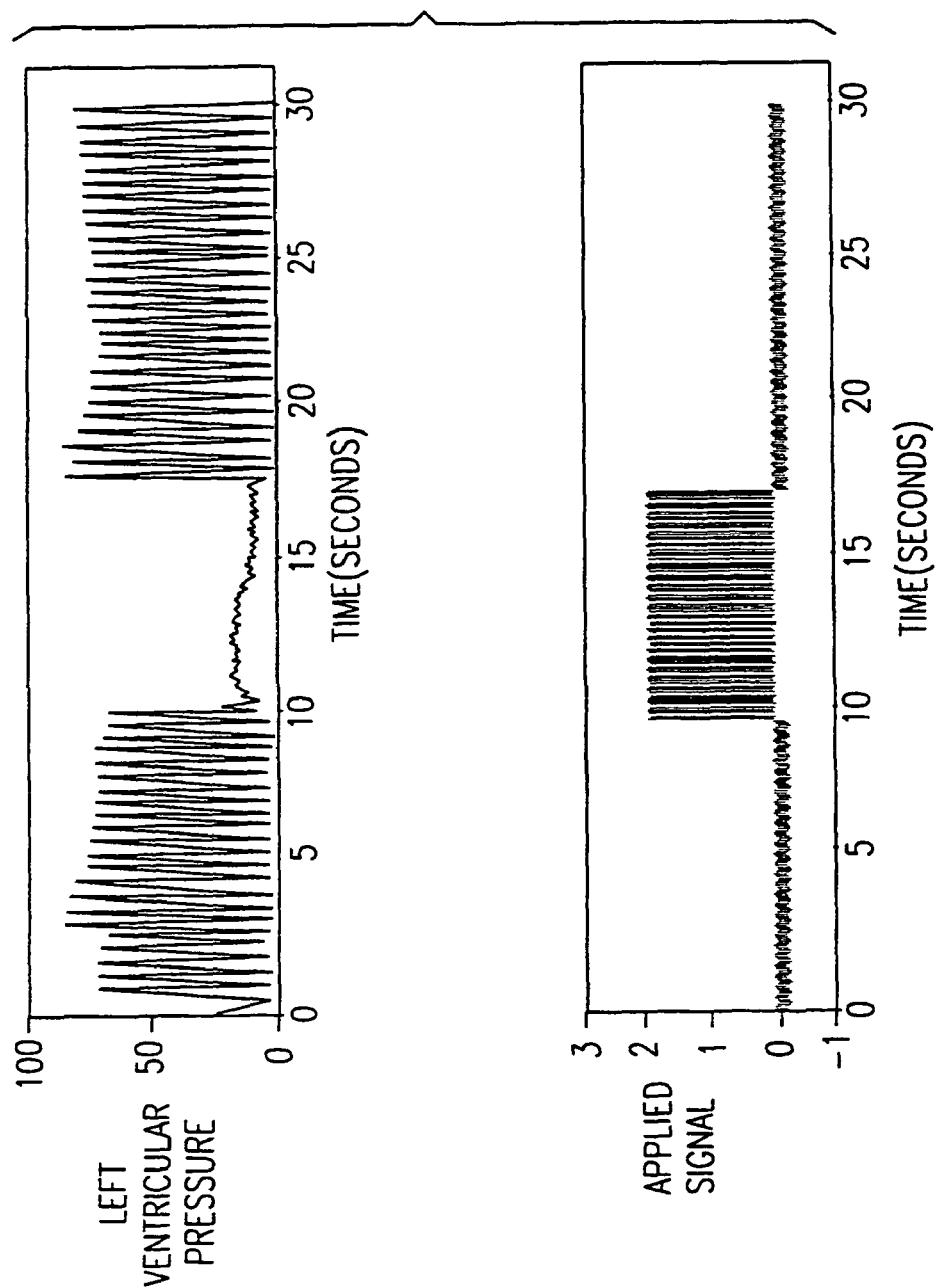
FIG. 9 schematically illustrates electrical signals applied to a beating dog heart, in accordance with a preferred embodiment of the present invention, and experimental results obtained thereby.

FIG. 9 schematically illustrates electrical signals applied to an in vivo dog's heart, in accordance with a preferred embodiment of the present invention, and experimental results obtained thereby. During a control period lasting approximately 8 seconds, the LVP is seen to be generally stable. Thereafter, the application of rapid pulses as provided by preferred embodiments of the present invention is associated with a marked drop in the LVP within 2 seconds from the initiation of the rapid pulses. Termination of rapid pulse application approximately 8 seconds from the initiation thereof is associated with a resumption of normal LVP within 2 seconds. FIG. 9 thus demonstrates the ability to control a global heart parameter using signals provided by preferred embodiments of the present invention. Such signals can be used to induce and terminate global capture within very short respective time periods, typically about 2 seconds. It is noted that no other defibrillation method known in the art has this capability.

FIG. 10 schematically illustrates an electrical signal applied to a beating, in vivo, pig heart, in accordance with a preferred embodiment of the present invention, and experimental results obtained thereby. In this experiment, a 60 Hz, 1 mA peak-to-peak square wave signal was applied for 800 milliseconds, through a bipolar electrode pair coupled to the anterior left ventricle. Electrical behavior of the heart was measured by externally-placed electrocardiographic (ECG) electrodes and by local sense electrodes, placed on the left ventricle. Additionally, the left ventricular pressure was measured throughout the duration of the experiment. Following application of the square wave signal, a 2 mA DC fencing signal was applied to the heart. Measurements shown in FIG. 10 demonstrate an electrical response to the applied signal within 250 ms of its initiation, and a mechanical response (the essentially complete cessation of left ventricular function) within 500 milliseconds. Normal cardiac function is seen to resume within 800 milliseconds of termination of the square wave signal.

FIG. 11 schematically illustrates an electrical signal applied to a beating pig heart, in accordance with a preferred embodiment of the present invention, and experimental results obtained thereby. In this experiment, a 15 Hz, 700 millisecond, 0.5 mA peak-to-peak square wave was applied in three consecutive bursts, separated by 300 milliseconds. The first burst induced an arrhythmia which looked like ventricular fibrillation, and captured the heart. Termination of the three bursts released the heart, whereupon the arrhythmia resolved, and normal cardiac activity resumed within approximately 500 milliseconds. It is believed that application of such signals to a heart already in fibrillation will similarly resolve the fibrillation within several seconds.

By contrast to the 5-15 joule shocks applied during a 10 millisecond period according to conventional defibrillation techniques, the defibrillation signal utilized in this experiment delivered, per electrode, less than 10 millijoules to the heart during a period greater than 100 times as long. Because the peak rate of energy transfer to the heart during defibrillation, as provided by these embodiments of the present invention, is approximately two to five orders of magnitude smaller than that utilized in the prior art, it is believed that shockless defibrillation provided by these embodiments is substantially safer and less traumatic than prior art defibrillation techniques. It is noted that prior art defibrillation techniques are unable to safely and effectively terminate ventricular fibrillation using shocks of significantly less than 5-15 joules. These techniques usually apply the energy over a period of less than 10 milliseconds. Thus, the peak rate of energy transfer to the heart associated with these techniques is typically above 500 W. Preferred embodiments of the present invention generally apply energy to the heart at a peak rate of less than about 100 W, and, as in the experiment shown in FIG. 11, can be successfully implemented using energy transfer rates significantly lower than 10 W (e.g., 10-100 mW).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

The invention claimed is:

1. A method comprising:
   determining that fibrillation is occurring in a heart of a person;
   defibrillating the heart without applying shock pulses by:
      applying electrical pulses to the heart at a rate greater than about 10 Hz, with a peak power that is less than about 100 W, wherein applying the pulses comprises applying a pulse having an amplitude less than about 50 mA, and
      terminating the electrical pulses, whereby the steps of applying and terminating the electrical pulses effectuate defibrillation of the heart;
   sensing motion of the heart, wherein applying the pulses comprises modifying a characteristic of at least some of the pulses applied to the heart responsive to the sensed motion; and
   pacing the heart at approximately 1 Hz while applying the electrical pulses at the rate greater than about 10 Hz.

2. A method comprising:
   determining that fibrillation is occurring in a heart of a person;
   defibrillating the heart without applying shock pulses by:
      applying electrical pulses to the heart at a rate greater than about 10 Hz, with a peak power that is less than about 100 W, wherein applying the pulses comprises applying a pulse having an amplitude less than about 50 mA, and
      terminating the electrical pulses, whereby the steps of applying and terminating the electrical pulses effectuate defibrillation of the heart;
   inhibiting propagation of an activation wave in the heart while applying the electrical pulses, by applying a fencing signal to the heart; and
   pacing the heart at approximately 1 Hz while applying the electrical pulses at the rate greater than about 10 Hz.

3. A method comprising:
   determining that fibrillation is occurring in a heart of a person;
   defibrillating the heart without applying shock pulses by:
      applying electrical pulses to the heart at a rate greater than about 10 Hz, with a peak power that is less than about 100 W, wherein applying the pulses comprises applying a pulse having an amplitude less than about 50 mA, and
      terminating the electrical pulses, whereby the steps of applying and terminating the electrical pulses effectuate defibrillation of the heart; and
   pacing the heart at approximately 1 Hz while applying the electrical pulses at the rate greater than about 10 Hz.

4. A method comprising:
   determining that fibrillation is occurring in a heart of a person; and
   defibrillating the heart without applying shock pulses by:
      applying electrical pulses to the heart at a rate greater than about 10 Hz, with a peak power that is less than about 100 W, wherein applying the pulses comprises applying a pulse having an amplitude less than about 50 mA, and
      terminating the electrical pulses, whereby the steps of applying and terminating the electrical pulses effectuate defibrillation of the heart,
   wherein applying the pulses comprises applying respective signals at a plurality of sites on the heart;
   wherein applying the signals comprises applying a first waveform at a first one of the sites and applying a second waveform, which differs from the first waveform, at a second one of the sites; and
   pacing the heart at approximately 1 Hz while applying the electrical pulses at the rate greater than about 10 Hz.

5. A method comprising:
   determining that fibrillation is occurring in a heart of a person; and
   defibrillating the heart without applying shock pulses by:
      applying electrical pulses to the heart at a rate greater than about 10 Hz, with a peak power that is less than about 100 W, wherein applying the pulses comprises applying a pulse having an amplitude less than about 50 mA, and
      terminating the electrical pulses, whereby the steps of applying and terminating the electrical pulses effectuate defibrillation of the heart,
   wherein applying the pulses comprises inducing depolarization in at least a region of the heart by applying the pulses;
   wherein applying the pulses comprises inducing a depolarization of substantially all excitable contractile tissue of the heart by applying the pulses; and
   pacing the heart at approximately 1 Hz while applying the electrical pulses at the rate greater than about 10 Hz.

6. A method comprising:
   determining that ventricular fibrillation is occurring in a heart of a person; and
   defibrillating the heart without applying shock pulses by:

applying an electrical signal to the heart with a total energy of no more than about 1 joule, and terminating the electrical signal, whereby the steps of applying and terminating the electrical signal effectuate defibrillation of the heart, wherein applying the signal comprises applying the signal in two or more bursts of signal application; and pacing the heart at approximately 1 Hz while applying the electrical signal.

7. A method comprising:

determining that ventricular fibrillation is occurring in a heart of a person;

defibrillating the heart without applying shock pulses by:
applying an electrical signal to the heart with a total energy of no more than about 1 joule, and
terminating the electrical signal, whereby the steps of applying and terminating the electrical signal effectuate defibrillation of the heart; and pacing the heart at approximately 1 Hz while applying the electrical signal.

8. A method comprising:

determining that ventricular fibrillation is occurring in a heart of a person; and defibrillating the heart without applying shock pulses by:
applying an electrical signal to the heart with a total energy of no more than about 1 joule, and
terminating the electrical signal, whereby the steps of applying and terminating the electrical signal effectuate defibrillation of the heart, wherein applying the signal comprises applying respective signals at a plurality of sites on the heart, wherein applying the signals comprises applying a first waveform at a first one of the sites and applying a second waveform, which differs from the first waveform, at a second one of the sites; and pacing the heart at approximately 1 Hz while applying the electrical signal.

9. A method comprising:

determining that ventricular fibrillation is occurring in a heart of a person; and defibrillating the heart without applying shock pulses by:
applying an electrical signal to the heart with a total energy of no more than about 1 joule, and
terminating the electrical signal, whereby the steps of applying and terminating the electrical signal effectuate defibrillation of the heart, wherein applying the signal comprises applying to the heart electrical pulses at a first frequency, wherein terminating the electrical signal comprises reducing the frequency to a second frequency; and pacing the heart at approximately 1 Hz while applying the electrical signal.

10. Apparatus for defibrillating a heart of a person, comprising:

one or more electrodes, adapted to be coupled to the heart;

a control unit, adapted to determine that fibrillation is occurring in the heart, and defibrillate the heart without applying shock pulses by:
driving the electrodes to apply electrical pulses to the heart at a rate greater than about 10 Hz, with a peak power that is less than about 100 W, wherein the control unit is adapted to drive at least one of the electrodes to apply a pulse having an amplitude less than about 50 mA, and
terminating the electrical pulses, whereby the applying and terminating of the electrical pulses effectuates defibrillation of the heart;

a sensor, adapted to sense motion of the heart and to convey a sensor signal responsive thereto to the control unit, wherein the control unit is adapted to modify a characteristic of at least some of the pulses applied to the heart responsive to the sensor signal; and a pacing electrode, adapted to be coupled to the heart, wherein the control unit is adapted to drive the pacing electrode to pace the heart at approximately 1 Hz, while concurrently driving the one or more electrodes to apply the electrical pulses.

11. Apparatus for defibrillating a heart of a person, comprising:

one or more electrodes, adapted to be coupled to the heart;

a control unit, adapted to determine that fibrillation is occurring in the heart, and defibrillate the heart without applying shock pulses by:
driving the electrodes to apply electrical pulses to the heart at a rate greater than about 10 Hz, with a peak power that is less than about 100 W, wherein the control unit is adapted to drive at least one of the electrodes to apply a pulse having an amplitude less than about 50 mA, and
terminating the electrical pulses, whereby the applying and terminating of the electrical pulses effectuates defibrillation of the heart;

a fencing electrode, adapted to be coupled to the heart, wherein the control unit is adapted to drive the fencing electrode to inhibit propagation of an activation wave in the heart, by applying a fencing signal to the heart, while concurrently driving the one or more electrodes to apply the electrical pulses; and a pacing electrode, adapted to be coupled to the heart, wherein the control unit is adapted to drive the pacing electrode to pace the heart at approximately 1 Hz, while concurrently driving the one or more electrodes to apply the electrical pulses.

12. Apparatus for defibrillating a heart of a person, comprising:

one or more electrodes, adapted to be coupled to the heart;

a control unit, adapted to determine that fibrillation is occurring in the heart, and defibrillate the heart without applying shock pulses by:
driving the electrodes to apply electrical pulses to the heart at a rate greater than about 10 Hz, with a peak power that is less than about 100 W, wherein the control unit is adapted to drive at least one of the electrodes to apply a pulse having an amplitude less than about 50 mA, and
terminating the electrical pulses, whereby the applying and terminating of the electrical pulses effectuates defibrillation of the heart; and a pacing electrode, adapted to be coupled to the heart, wherein the control unit is adapted to drive the pacing electrode to pace the heart at approximately 1 Hz, while concurrently driving the one or more electrodes to apply the electrical pulses.

13. Apparatus for defibrillating a heart of a person, comprising:

one or more electrodes, adapted to be coupled to the heart; and a control unit, adapted to determine that fibrillation is occurring in the heart, and defibrillate the heart without applying shock pulses by:
driving the electrodes to apply electrical pulses to the heart at a rate greater than about 10 Hz, with a peak power that is less than about 100 W, wherein the control unit is adapted to drive at least one of the electrodes to apply a pulse having an amplitude less than about 50 mA, and terminating the electrical pulses, whereby the applying and terminating of the electrical pulses effectuates defibrillation of the heart, wherein the one or more electrodes comprise first and second electrodes, and wherein the control unit is adapted to drive the first electrode to apply a first waveform at a first site of the heart, and is adapted to drive the second electrode to apply a second waveform, which differs from the first waveform, at a second site of the heart; and a pacing electrode, adapted to be coupled to the heart, wherein the control unit is adapted to drive the pacing electrode to pace the heart at approximately 1 Hz, while concurrently driving the one or more electrodes to apply the electrical pulses.

* * * * *